United States Patent
Powers

(10) Patent No.: US 6,784,568 B2
(45) Date of Patent: Aug. 31, 2004

(54) DEVICE WITH MULTIPLE, CONCURRENTLY-INSTALLED POWER MODULES AND METHOD FOR CONTROLLING SAME

(75) Inventor: Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/414,919

(22) Filed: Apr. 16, 2003

(65) Prior Publication Data

US 2003/0193245 A1 Oct. 16, 2003

Related U.S. Application Data

(62) Division of application No. 09/610,634, filed on Jul. 5, 2000, now Pat. No. 6,586,850.

(51) Int. Cl.[7] .................................................. H02J 7/00
(52) U.S. Cl. .......................................... 307/66; 320/112
(58) Field of Search .................... 307/66, 150; 320/112, 320/114

(56) References Cited

U.S. PATENT DOCUMENTS

| | | | | |
|---|---|---|---|---|
| 4,080,558 A | | 3/1978 | Sullivan ....................... 320/39 |
| 4,709,202 A | * | 11/1987 | Koenck et al. | |
| 4,835,410 A | * | 5/1989 | Bhagwat et al. | |
| 4,847,513 A | * | 7/1989 | Katz et al. | |
| 5,235,979 A | | 8/1993 | Adams ........................... 607/5 |
| 5,372,605 A | | 12/1994 | Adams et al. .................. 607/5 |
| 5,483,165 A | | 1/1996 | Cameron et al. ............ 324/427 |
| 5,625,291 A | | 4/1997 | Brink et al. .................. 324/427 |
| 5,640,078 A | | 6/1997 | Kou et al. ..................... 320/15 |
| 5,661,392 A | * | 8/1997 | Imazeki | |
| 5,721,482 A | | 2/1998 | Benvegar et al. .............. 320/43 |
| 5,800,460 A | | 9/1998 | Powers et al. .................. 607/5 |
| 5,868,794 A | | 2/1999 | Barkley et al. ................. 607/5 |
| 5,879,374 A | | 3/1999 | Powers et al. .................. 607/5 |
| 5,889,388 A | | 3/1999 | Cameron et al. ............ 320/166 |
| 5,899,925 A | | 5/1999 | Ochs et al. ..................... 607/5 |
| 5,920,178 A | * | 7/1999 | Robertson, Jr. et al. | |
| 5,929,764 A | | 7/1999 | Brink et al. ................. 340/636 |
| 6,037,750 A | * | 3/2000 | Von Novak | |
| 6,163,131 A | * | 12/2000 | Gartstein et al. | |
| 6,586,850 B1 | * | 7/2003 | Powers | |

OTHER PUBLICATIONS

"DS2434 Battery Identification Chip," Dallas Semiconductor Corporation, pp. 1–20, Nov. 20, 1999.
"Programming DS234X Battery Identification Chips," Tech. Brief No. 5, Dallas Semiconductor Corporation, pp. 1–9, Oct. 31, 1999.

* cited by examiner

Primary Examiner—Gregory J. Toatley, Jr.
(74) Attorney, Agent, or Firm—Tony E. Piotrowski

(57) ABSTRACT

A device such as an electrotherapy device implementing the invention includes multiple power module receptacles each of which is configured to received at least one type of power module, and a power management system that selectively routes power provided by one or more installed power modules to the device components and, preferably, to other power module receptacles. The types of power modules that operate in the power module receptacles include, for example, rechargeable battery packs, non-rechargeable battery packs and AC power packs. Preferably these power modules are each fully integrated, functionally self-contained power modules. For example, the rechargeable battery pack includes a charge controller specifically designed to charge the battery pack in which it is implemented.

5 Claims, 10 Drawing Sheets

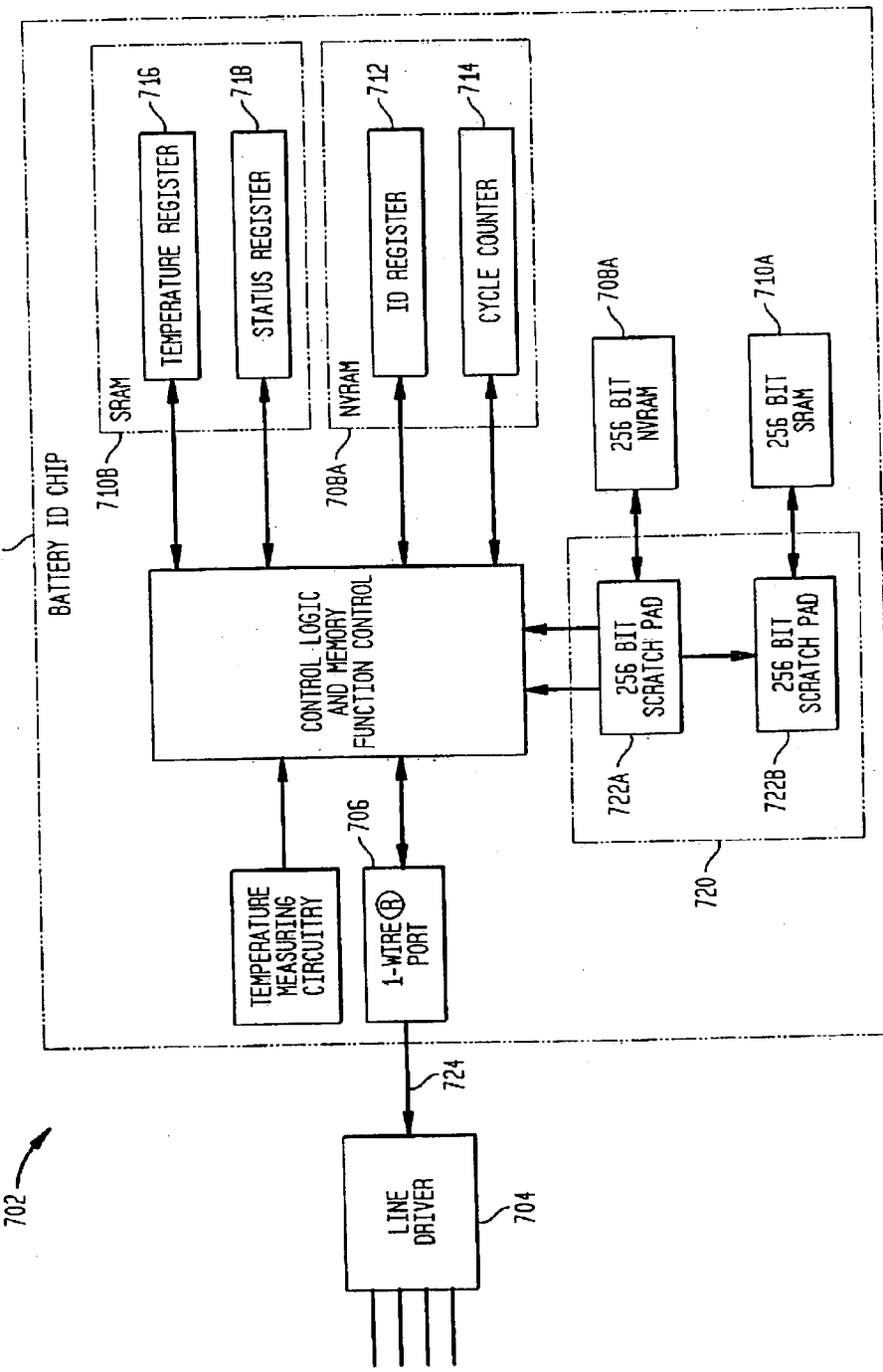

FIG. 9

| 122A<br>POWER MODE<br>RECEPTACLE | 122B<br>POWER MODE<br>RECEPTACLE |
|---|---|
| 901 — AC POWER PACK 322 | RECHARGEABLE BATTERY PACK 302 |
| 902 — AC POWER PACK 322 | NON-RECHARGEABLE BATTERY PACK 342 |
| 903 — RECHARGEABLE BATTERY PACK 302 | RECHARGEABLE BATTERY PACK 302 |
| 904 — RECHARGEABLE BATTERY PACK 302 | NON-RECHARGEABLE BATTERY PACK 342 |
| 905 — NON-RECHARGEABLE BATTERY PACK 342 | RECHARGEABLE BATTERY PACK 302 |
| 906 — NON-RECHARGEABLE BATTERY PACK 342 | NON-RECHARGEABLE BATTERY PACK 342 |

DEVICE WITH MULTIPLE, CONCURRENTLY-INSTALLED POWER MODULES AND METHOD FOR CONTROLLING SAME

RELATED APPLICATIONS

This application is a divisional application of U.S. patent application Ser. No. 09/610,634, filed on Jul. 5, 2000, now U.S. Pat. No. 6,586,850.

The following applications are related to the present application and are incorporated by reference herein and elsewhere in this application: U.S. Pat. No. 5,607,454 to Cameron et al., entitled "Electrotherapy Method and Apparatus;" U.S. Pat. No. 5,800,460 to Powers et al., entitled "Method For Performing Self-Test in a Defibrillator;" U.S. Pat. No. 5,879,374 to Powers et al., entitled "External Defibrillator With Automatic Self-Testing Prior to Use;" U.S. patent application Ser. No. 09/191,685, entitled "Battery Pack Chemistry Detection and Identification System and Method," filed Nov. 13, 1998; U.S. patent application Ser. No. 09/192,116, entitled "System and Method for Detecting Performance Components of a Battery Pack," filed Nov. 13, 1998; U.S. Pat. No. 5,483,165 to Cameron et al., entitled "Battery System and Method For Determining A Battery Condition;" U.S. patent application Ser. No. 09/184,485 filed Nov. 2, 1998 under attorney docket no. 10980507-1, entitled "A Conforming Intelligent Battery Label;" U.S. Pat. No. 5,591,213 to Morgan, entitled "Defibrillator System Condition Indicator;" and, U.S. Pat. No. 5,611,815 to Cole et al., entitled "Defibrillator with Training Features."

BACKGROUND OF THE INVENTION

1. Field of the Invention

The present invention relates generally to power modules and, more particularly, to systems and methods for providing power to battery-powered devices.

2. Related Art

Electrotherapy devices are used to provide electrical shocks to treat patients for a variety of heart arrhythmias. For example, external defibrillators typically provide relatively high-energy shocks to a patient as compared to implantable defibrillators, usually through electrodes attached to the patient's torso. External defibrillators are used to convert ventricular fibrillation or shockable tachycardia to a normal sinus rhythm. Similarly, external cardioverters can be used to provide shocks to convert atrial fibrillation to a more normal heart rhythm.

Conventional external defibrillators have been used primarily in hospitals and other medical care facilities. In such environments, the frequency with which a particular defibrillator is operated, referred to herein as the use model of the device, is significant, perhaps on the order of several times per week. While these external defibrillators have been known for years, generally they have been large and expensive, making them unsuitable for use outside of a medical facility. More recently, portable external defibrillators for use by emergency medical service (EMS) and other medically-trained first responders have been developed. These defibrillators allow medical care to be provided to a victim at the victim's location considerably earlier than hospital defibrillators, increasing the likelihood of survival. To operate effectively in the intended mobile environment, portable defibrillators require a portable energy source. Several defibrillator and after-market manufacturers have provided battery packs for such defibrillators. These battery packs, which have traditionally been rechargeable due to the anticipated high frequency use model, are available with different chemistries such as lead acid, nickel cadmium, lithium ion and the like.

With recent advances in technology, portable defibrillators have become more automated, allowing even minimally trained operators to use such devices to aid a victim in the critical first few minutes subsequent to the onset of sudden cardiac arrest. Such portable defibrillators, referred to as automatic or semi-automatic external defibrillators (generally, AEDs), may be stored in an accessible location in a business, home, aircraft or the like. Due to the anticipated low use model of such defibrillators, as well as the increased diligence required of rechargeable battery packs, many conventional AEDs operate with a non-rechargeable battery pack. This is more common in recent history due to advances in battery technology that has facilitated the development of long life, high capacity, non-rechargeable battery packs.

One particular problem that arises using currently available portable defibrillators is that occasionally it may be necessary or desirable to operate the device in accordance with a use model different than that for which the defibrillator was originally designed. Currently available defibrillators are not amenable to accommodating changes in the use model by enabling the user to change the power source. One characteristic of defibrillators that prevents such a change in operation is the use of a charge controller in the defibrillator that implements a charging protocol to charge an battery pack while the battery pack is installed. Such charge controllers implement a single charging protocol suitable for charging a battery pack having cells of a specific chemistry. As a result, the charge controller selected when the defibrillator is manufactured is based on the chemistry of the rechargeable battery pack specified for use with the defibrillator. Thereafter, the defibrillator is restricted to using battery packs of the type and chemistry that can be charged by the implemented charge controller. This, in turn, makes it undesirable to operate the defibrillator in accordance with a use model other than that which the defibrillator was originally designed. On the one hand, the use of a high maintenance, rechargeable battery pack in a low use model is impracticable. Conversely, the use of a non-rechargeable battery pack in a high use model environment is prohibitively expensive.

What is needed, therefore, is a flexible approach for providing power to an electrotherapy device that does not restrict the type and chemistry of the battery packs with which it operates, and which can be configured to accommodate different device operations.

SUMMARY OF THE INVENTION

A number of embodiments of the invention are summarized below. It should be understood that the summarized embodiments are not necessarily inclusive or exclusive of each other and may be combined in any manner in connection with the same or different embodiments that is non-conflicting and otherwise possible. These disclosed embodiments of the invention, which are directed primarily to systems and methods related to power modules and devices that operate with such power modules, are exemplary embodiments only and are also to be considered non-limiting.

A device such as an electrotherapy device implementing the power management system of the present invention includes multiple power module receptacles each of which is configured to have installed therein at least one type of power module. A power distribution system selectively routes power provided by one or more installed power modules to components of the electrotherapy device. The types of power modules that operate in the power module receptacles include, for example, rechargeable battery packs, non-rechargeable battery packs and AC power packs. Selection of which power module is to be installed to provide power to the device at any given time may be determined based on various factors such as the status and capacity of the power modules, the anticipated use model of the device, etc. Advantageously, any combination of power modules may be concurrently installed in the power module receptacles to optimally support the anticipated use model of the device. In addition, as the use model of the device changes, so too can the installed power module selected to power the device.

Preferably the power distribution system also routes power between power module receptacles that include fully integrated, functionally self-contained power modules. For example, the rechargeable battery pack preferably includes a charge controller specifically designed to charge the battery pack in which it is implemented. This enables an AC power module and such a rechargeable battery pack to be concurrently installed in the device, connected to each other to enable the AC power pack to charge the rechargeable battery pack. This provides the significant advantage of eliminating the need to include an equivalent charge controller in the device itself.

In one embodiment, the power distribution system includes an internal network of power distribution buses that can be selectively connected to specified power module receptacles and device components. Independently controlled switches constructed and arranged to connect individual power modules to specific power distribution buses are also included. A power distribution manager may be implemented to determine a power management configuration and to control the switches to electrically connect specified power modules and device components to implement the power management configuration. The power management configuration may be determined based on any number of factors such as the intended use model of the device, the type of power modules installed in the power module receptacles, and an ability of the installed power modules to support the use model of the device.

In another embodiment of the invention, an electrotherapy device such as a portable defibrillator is disclosed. The device includes first and second power module receptacles. The first power module receptacle is configured to have installed therein a power module of a first power module type. The second power module receptacle is configured to have installed therein a power module of a second power module type. The device also includes an internal power distribution network configured to connect one or more of the installed power modules to device components. Individually controlled switches can be activated to electrically connect installed power modules to one or more power buses. A power management system controls the switches to connect selected installed power modules to the power distribution network.

In a further embodiment of the invention, a rechargeable battery pack is disclosed. The battery pack includes a housing with at least one battery cell and a charge controller mounted therein. The charge controller charges the battery cell using an externally-applied DC power. The battery cell may be of a particular chemistry while the charge controller is configured to charge battery cells of such particular battery chemistry. The chemistry of the battery cells may be, for example, lithium ion, lead acid, NiCd, etc.

In a still further embodiment of the invention, a set of power modules each configured to provide a DC voltage to a device when operationally installed therein is disclosed. In one embodiment, the set of power modules includes a rechargeable battery pack and a non-rechargeable battery pack. The rechargeable battery pack includes a first housing with one or more battery cells and a battery charger mounted therein. The battery charger applies to the battery cells a charging voltage derived from an externally-applied DC voltage. The battery cells generate a first DC voltage for use by the device. The non-rechargeable battery pack includes a second housing with one or more battery cells mounted therein. These battery cells generate a second DC voltage for use by the device. Preferably, the set of power modules also includes an AC power pack. The AC power pack includes a third housing, an AC-to-DC converter mounted within the third housing, and an electrical interface for providing an externally-applied AC voltage to the AC-to-DC converter. The AC-to-DC converter converts the applied AC voltage to a third DC voltage suitable for use by the device. In one embodiment, the first, second and third housings have a same form factor.

Various embodiments of the present invention provide certain advantages and overcome certain drawbacks of the conventional powered devices, particularly, electrotherapy devices. Not all embodiments of the invention share the same advantages and those that do may not share them under all circumstances. This being said, embodiments of the present invention provides numerous advantages some of which are noted above. These and other features and advantages of the present invention as well as the structure and operation of various embodiments of the present invention are described in detail below with reference to the accompanying drawings.

BRIEF DESCRIPTION OF THE DRAWINGS

The above and further advantages of the invention will be more clearly appreciated from the following detailed description when taken in conjunction with the accompanying drawings, in which like reference numerals indicate like structures or method steps, in which the left-most one or two numerals of a reference numeral indicate the number of the figure in which the referenced element first appears, and in which:

FIG. 7 is an schematic diagram of the smart interface implemented in the power modules illustrated in FIG. 1.

FIG. 9 is a table illustrating the possible combinations of power modules that may be installed in the power module receptacles of the electrotherapy device illustrated in FIG. 1.

DETAILED DESCRIPTION

Figure 1:
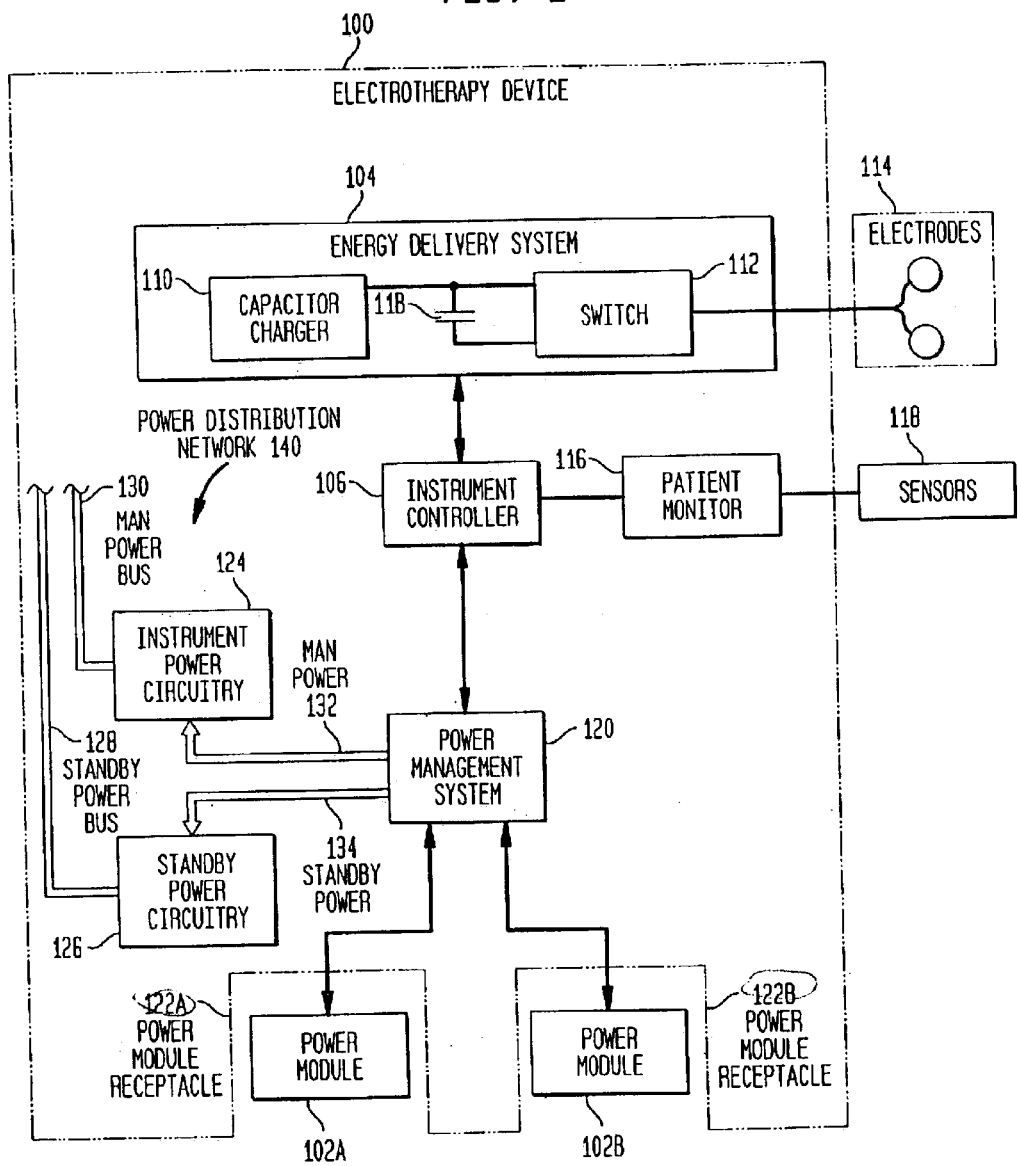
FIG. 1 is a simplified block diagram of an exemplary electrotherapy device implementing a power management system in accordance with one embodiment of the present invention.

Embodiments of the present invention will be described herein with reference to a particular type of battery-powered device commonly known as an electrotherapy device. FIG. 1 is a simplified block diagram of an exemplary electrotherapy device 100. Electrotherapy device 100 may include the necessary components to defibrillate, cardiovert or pace a patient, or to perform any combination of such operations. It should be appreciated that since such devices are well known in the art, components described herein and illustrated in FIG. 1 are exemplary only. In the following description it is envisioned that electrotherapy device 100 is a portable defibrillator such as the many models of portable and transportable defibrillators available from Agilent Technologies, Inc., Palo Alto, Calif.

Components of electrotherapy device 100 operate under the control of a instrument controller 106. Controller 106 may be embodied in a microprocessor, gate array, ASIC, or other control logic architecture, as well as any combination thereof. Preferably, controller 106 is implemented in software code that is executed on a commercially available microprocessor. Generally, such software code is stored in a memory device (not shown) accessible by such a microprocessor.

Electrotherapy device 100 includes an energy delivery system 104 that delivers energy to a patient (not shown). Energy delivery system 104 is connected to electrodes 114 and includes generally a capacitor or capacitor bank 108, a capacitor charger 110 and a switching mechanism 112. In response to controller 106, capacitor charger 104 charges capacitor 108 and energy delivery system 104 delivers an electric shock from capacitor 108 to electrodes 114 that are placed on a patient's chest.

Patient monitor 116 monitors the patient's heart rhythm and determines whether the monitored rhythm is shockable. Patient monitor 116 receives information from sensors 118, which may be integrated in electrodes 114, physically separate devices or a combination thereof. Patient monitor 116 communicates a shock decision to instrument controller 106. Energy delivery system 104 then delivers a therapeutic energy pulse to the patient via electrodes 114.

These and other components of electrotherapy device 100 are well known in the art. Electrotherapy devices suitable for implementing the present invention may include the same or similar device components now or later developed. The above and other device components not specifically described in this application may be included and configured to operate in the manner described, for example, in U.S. Pat. No. 5,607,454 to Cameron et al., entitled "Electrotherapy Method and Apparatus," the disclosure of which is incorporated herein by reference in its entirety.

In this illustrative embodiment, electrotherapy device 100 includes two power module receptacles 122A and 122B. Power module receptacles 122A, 122B are configured to operationally receive a power module 102A, 102B, respectively. In this illustrative embodiment, power for device 100 is provided only by installed power modules 102. Thus, at least one power module 102 needs to be installed in a power module receptacle 122 to provide power to electrotherapy device 100. It should become apparent from the present disclosure, however, that power modules 102 may supplement another source of power such as a permanent AC power plug. This will be described in greater detail below. It should also be appreciated that two power modules and power module receptacles are set forth in the embodiment shown in FIG. 1 for illustrative purposes only; embodiments of the present invention may implement any number of concurrently installed power modules 102.

As will be described in greater detail below, in one embodiment of the invention, power modules 102 may include any type of battery pack now or later developed that provides power characteristics suitable for electrotherapy device 100. These include non-rechargeable or rechargeable battery packs of any chemistry. In addition, power modules 102 may include an AC power pack that receives and converts AC power to a DC power suitable for powering all or part of electrotherapy device 100. In one embodiment, power modules 102 have the same electrical and mechanical interface; that is, the same form factor, allowing any power module 102 to be installed in any receptacle 122. That is, power modules 102 are interchangeable with respect to power module receptacles 122A, 122B. In an alternative embodiment, power module receptacles 122A, 122B are each specifically configured to received a particular type of power module 102; that is, a rechargeable battery pack, a non-rechargeable battery pack or an AC power pack.

As will be described in detail below, in certain embodiments of the invention, each power module 102 preferably includes the.,functionality necessary to enable it to operate as a DC power source for electrotherapy device 100. That is, power modules 102 may be functionally self-contained modules that, although possibly larger and more complex than conventional battery packs, eliminate the need to include supporting components in electrotherapy device 100. For example, the rechargeable battery pack may include a charge controller suitable for charging the battery cells of that battery pack. This eliminates the need to include such a charge controller in electrotherapy device 100.

In accordance with one embodiment of the invention, electrotherapy device 100 includes a power distribution network 140 that receives power from an installed power module 102 and selects a power source based on operational conditions of electrotherapy device 100. Power distribution network 140 includes a conventional DC power bus to distribute main instrument power, referred to herein as main power bus 130. A standby power bus 128 may also be included. Standby power bus 128 distributes power to certain select components of electrotherapy device 100 when electrotherapy device 100 is not operationally powered. This enables standby power to be provided continually to certain device components. This insures that certain operations can be performed regardless of whether electrotherapy device 100 is deployed and operational.

Power distribution network 140 also includes instrument power circuitry 124 that receives power from an installed power module and performs various well known functions to filter and stabilize the power signal prior to allowing the power signal to travel over main power bus 130. Similarly, standby power circuitry 126 performs analogous operations for standby power bus 128. Circuitry 124, 126 are considered to be well known in the art and, therefore, are not described further herein.

In accordance with this embodiment of the present invention, a power management system 120 is included in electrotherapy device 100. Power management system 120 is operationally interposed between power distribution network 140 and power module receptacles 122. Power management system 120 preferably selects for connection to power distribution network 140 combinations of one or more installed power modules 102 to achieve a desired power configuration. Specifically, power management system 120 determines which power module 102 is to provide power to main power bus 130 and, in embodiments wherein device 100 includes a standby bus 128, to standby power bus 128. Further, power management system 120 may selectively interconnect two or more installed power modules 102. Importantly, in the event of a catastrophic failure of a power module during use, power management system 120 changes the installed power module 102 responsible for providing power to main power bus 130. As used herein, the term "power configuration" refers generally to the selected coupling of installed power modules 102 and one or more internal power buses.

Figure 2:
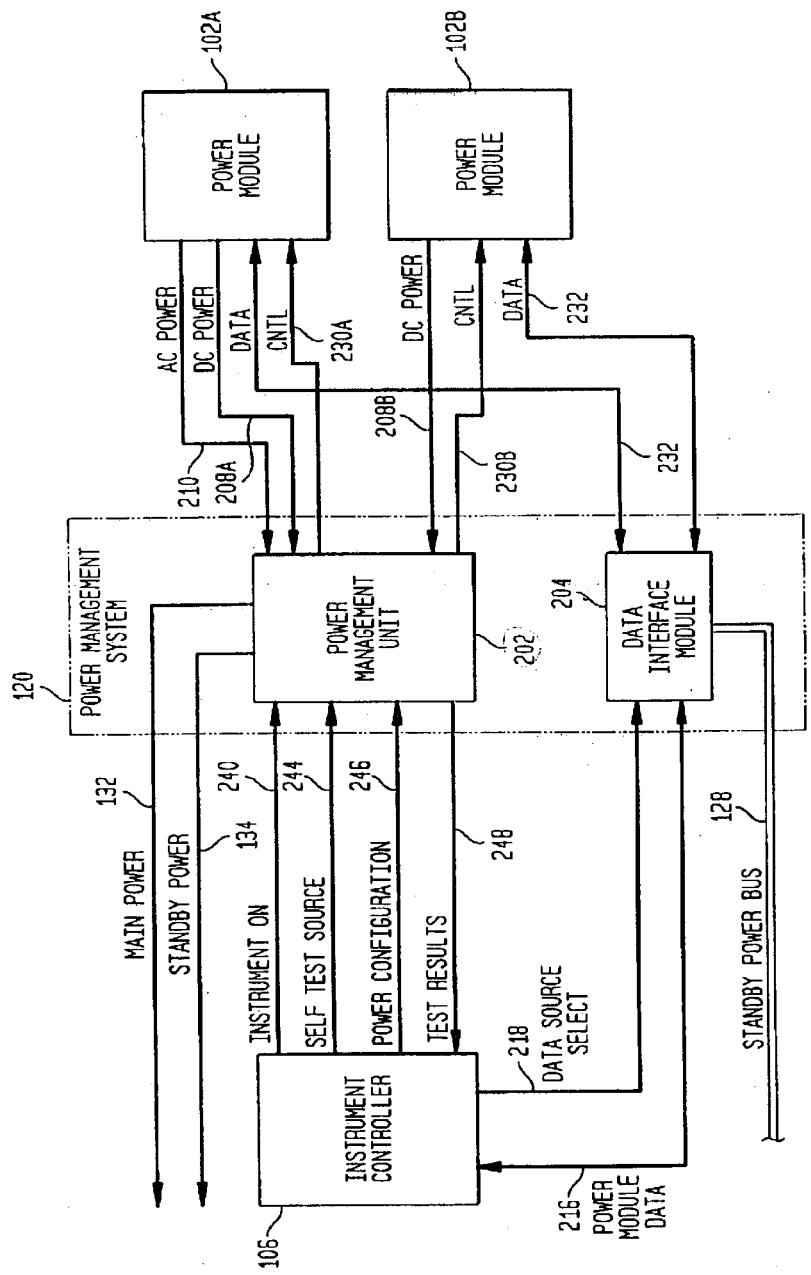
FIG. 2 is a high level functional block diagram of one embodiment of the power management system illustrated in FIG. 1.

FIG. 2 is a high-level functional block diagram of power management system 120 in accordance with one embodiment of the present invention. Power management system 120 includes two primary components: a power management unit 202 and a data interface module 204. Power management unit 202 receives power from each power module receptacle 122 via an electrical connection referred to herein as a power bus. The power buses over which power is provided to power management unit 202 for subsequent distribution includes an AC power bus 210 and a DC power bus 208A from power module 102A, and a DC power bus 208B from power module 102B. For reasons provided below, two power buses connect power module receptacle 122A and power management unit 202. This two bus configuration maximizes flexibility of the receptacle by providing one bus for use when an AC power pack is installed and another power bus for use when a battery pack is installed.

In the embodiment described herein, power management unit 202 selectively provides power from power modules 102 to internal main and standby power buses 132, 134 by selectively interconnecting power buses 208A, 208B and 210 with main and standby power buses 132, 134. In addition, power management system 120 may generate control commands 230A and 230B to power modules 102A and 120B. Control commands 230 may be used, for example, to cause power modules 102 to provide or cease providing AC power over bus 210 or DC power over buses 208A and 208B.

The power configuration may be determined based on the number, type, capacity and other characteristics of installed power modules 102, the power demands of electrotherapy device 100, the power demands of installed power modules 102, etc. In this illustrative embodiment, instrument controller 106 makes such a determination. Accordingly, the noted components of power management system 120 communicate with, and are responsive to, instrument controller 106. In particular, power management unit 202 implements a power configuration in response to commands and/or data received from instrument controller 106.

Specifically, power management unit 202 receives as an input an indication of whether electrotherapy device 100 is to be powered, referred to as "instrument on" signal 240. In this embodiment, instrument controller 106 generates signal 240. Any number of conditions may be taken into consideration by instrument controller 106 to determine the state of instrument on signal 240. In an alternative embodiment, power management unit 202 may receive such an indication directly from other components of electrotherapy device 100 such as a power switch.

Instrument controller 106 receives power module data 216 from power modules 102 through data interface module 204. Power module data 216 may include, for example, the type, chemistry and capacity of those power modules 102 that are battery packs, the availability of DC power from an installed AC power pack 322, etc. Other information may also be provided to instrument controller 106 for determining power configuration 246. For example, in certain embodiments, an operator's selected power configuration is considered.

Importantly, the above information may be used by instrument controller 106 to gain further insights into the power demands of electrotherapy device 100, as well as to obtain the availability of power from installed power modules 102. For example, the type of battery pack (rechargeable or non-rechargeable) may be used to infer the anticipated use model of electrotherapy device 100. Portable defibrillators that are used by emergency medical service (EMS) and other first responders may be operated a few times a week. Defibrillators having such a high use model are generally equipped to receive a rechargeable battery pack. More advanced defibrillators, such as AEDs, are installed in public facilities such as commercial aircraft, stadiums and the like. These defibrillators have a relatively low use model and are likely to be used infrequently as compared to their above-noted counterparts, perhaps once or twice per year. Such defibrillators are generally equipped to receive a non-rechargeable battery pack, which is best suited for such use models. Thus, the inclusion of the battery type in power module data 216 may provide instrument controller 106 with information from which it may infer whether electrotherapy device 100 is going to be used frequently or infrequently. One example of how instrument controller 106 may infer the use model from power module data 216 provided in a two module scenario is provided below in Table A.

TABLE A

| Power Module 102A | Power Module 102B | Use Model | Portability |
|---|---|---|---|
| AC Power Pack | — | High | Low |
| AC Power Pack | Rechargeable Battery Pack | High | Low |
| AC Power Pack | Non-rechargeable Battery Pack | High | Low |
| Rechargeable Battery Pack | — | High | Low |
| Rechargeable Battery Pack | Rechargeable Battery Pack | High | High |
| Rechargeable Battery Pack | Non-rechargeable Battery Pack | High | High |
| Non-rechargeable Battery Pack | — | Low | High |
| Non-rechargeable Battery Pack | Non-rechargeable Battery Pack | Low | High |

As will be appreciated by those of skill in the art, Table A is provided for illustrative purposes. Other inferences may be drawn without departing from the scope of the invention. For example, these inferences may not be wholly applicable in a three-module scenario.

As shown in FIG. 2, instrument controller 106 also provides power management unit 202 with a self-test source command 244. Typically, electrotherapy device 100 performs one or more self-tests to insure availability and reliability of electrotherapy device 100. For example, some of today's defibrillators implement one or more self-tests such as those as described in U.S. Pat. No. 5,800,460 to Powers et al., entitled "Method For Performing Self-Test in a Defibrillator" and U.S. Pat. No. 5,879,374 also to Powers et al., entitled "External Defibrillator With Automatic Self-Testing Prior to Use," the disclosures of which are incorporated by reference herein in their entirety. An important embodiment of such self-tests is the determination of the health and status of an installed power module 102. Toward that end, instrument controller 106 generates self-test source command 244 to identify which installed power module 102 is to provide power to either or both of the internal buses 134, 136 during a particular self-test. In addition, power management system 120 may also test installed power modules 102. In such embodiments, self-test source 244 may include an indication of which installed power module 102 power management system 120 is to test. The results of such tests are provided to instrument controller 106 via test results 248.

Data interface module 204 exchanges information with power modules 102 installed in power module receptacles 122. Data interface module 204 selects a data path 232A, 232B from power module receptacles 122A, 122B, respectively, in response to a data source select command 218 from instrument controller 106. Data interface module 204 then transfers power module data 216 to/from instrument controller 106. In this illustrative embodiment, data interface module 204 is powered by standby power and, thus, is connected to standby power bus 128.

Figure 3A:
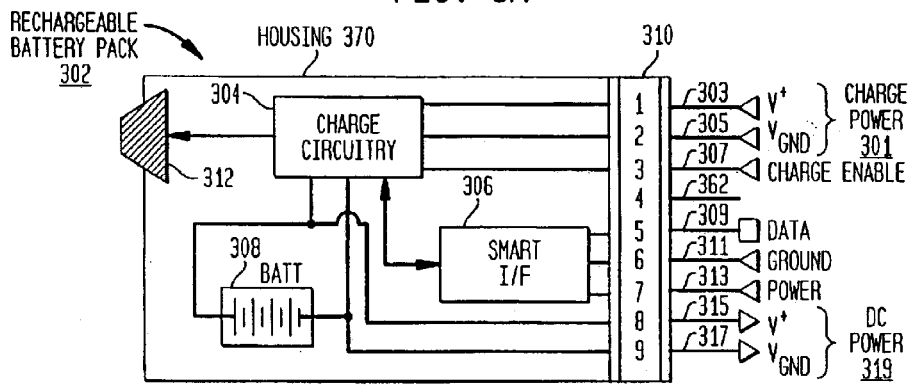
FIG. 3A is schematic block diagram of one embodiment of a rechargeable battery pack that may be used as a power module in accordance with certain embodiments of the present invention.
Figure 3B:
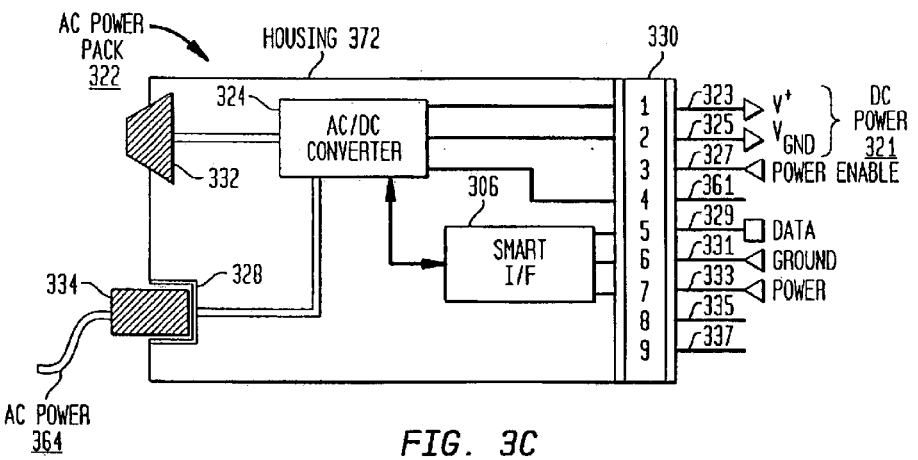
FIG. 3B is schematic block diagram of one embodiment of an AC power pack that may be used as a power module in accordance with certain embodiments of the present invention.
Figure 3C:
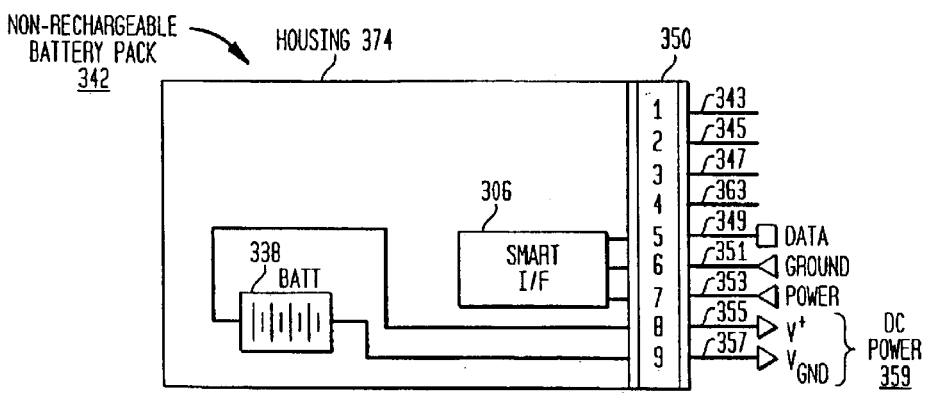
FIG. 3C is schematic block diagram of one embodiment of a non-rechargeable battery pack that may be used as a power module in accordance with certain embodiments of the present invention.

FIGS. 3A–3C are schematic diagrams of three different types of power modules 102 which may be installed in electrotherapy device 100 in accordance with one embodiment of the present invention. There are generally two types of power modules 102 that can be installed in electrotherapy device 100. The first type of power module includes those that provide energy storage, referred to herein as battery packs. The battery packs may be rechargeable, such as rechargeable battery pack 302 illustrated in FIG. 3A, or non-rechargeable such as non-rechargeable battery pack 342 illustrated in FIG. 3C. Rechargeable and non-rechargeable battery packs 302, 342 each generate a DC voltage suitable for use by electrotherapy device 100. The second type of power module includes those power modules that convert external AC power to DC power, referred to herein as AC power packs. An AC power pack 322 illustrated in FIG. 3B converts AC power to DC power suitable for use by electrotherapy device 100.

In accordance with one embodiment of the present invention, power modules 102 preferably provide all the necessary functionality associated with the storage of energy and the generation of DC power for electrotherapy device 100, including, as appropriate, the charging of rechargeable battery packs 302. Implementation of such functionally-contained power modules 102 provides many benefits. For example, electrotherapy device 100 need not include an AC-DC converter or a charge controller since both are implemented in the appropriate power module.

As shown schematically in FIGS. 3A–3C, rechargeable battery pack 302, AC power pack 322 and non-rechargeable battery pack 342 preferably have interchangeable electrical and mechanical interfaces; that is, the same form factor. Any type of power module may be installed in a device having a single power module receptacle 122 to provide the optimal power module for a given use model. In addition, in devices having more than one power module receptacle such as device 100, any power module may be installed in any receptacle in accordance with this embodiment of the invention. In the following description power modules 102 illustrated in FIGS. 3A–3C will be described as being configured for installation in power module receptacles 122 of electrotherapy device 100 illustrated in FIG. 1. However, the more common scenario would include having one receptacle capable of interacting with the AC power pack 322 while being flexible enough to connect with other power modules, while the other receptacles would be designed to receive either or both battery packs 302, 342.

Turning now to FIG. 3A, rechargeable battery pack 302 includes a battery 308 located within a housing 370. A charge controller 304, implemented as charge circuitry in FIG. 3A, is also located within housing 370. Charge controller 304 charges battery 308 using an externally-applied DC power 301. Preferably, a smart interface (I/F) 306 is also included to store data accessible to power management system 120. Battery pack 302 has an electrical interface 310 to electrically connect to electrotherapy device 100 when installed in a power module receptacle 122.

Battery 308 is formed from one or more battery cells of a particular rechargeable battery chemistry. Battery 302 may be, for example, lead acid, NiMH, lithium ion, or any other chemistry now or later developed. Two pins 8 and 9 are connected to positive and negative terminals of battery 308 to provide a positive voltage (V+) over line 315, and a ground voltage ($V_{GND}$) over line 317 to electrotherapy device 100. Together V+ and $V_{GND}$ comprise DC power 319. It should be understood that battery 308 might be of any configuration and chemistry now or later developed that is compatible with the teachings of the present invention.

In accordance with embodiments of the present invention, integrated charge circuitry 304 is configured to implement a charging protocol suitable for charging the chemistry of battery 308. Charge controller 304 may be any charge controller now or later developed suitable for charging the particular battery cells 308 implemented in battery pack 302. The construction and operation of charge circuitry 304 is well known in the art and is not described further herein.

Charge circuitry 304 has three pins allocated in electrical interface 310. At pin 1 an input line 303 provides a voltage signal $V^+$. Similarly, a ground voltage $V_{GND}$ is received at pin 2 over input line 305 and provided to charge circuitry 304. $V^+$ and $V_{GND}$ on lines 303, 305 together comprise charge power 301. In one embodiment, battery 308 is a 12-volt battery. Preferably, charge power 301 is approximately 15 volts to avoid the need to implement boost or buck converters to charge such a 12-volt battery 308.

When rechargeable battery pack 302 is inserted into a power module receptacle 122, $V^+$ input line 303 and $V_{GND}$ input line 305 are at times connected to a source of charge power 301. In one embodiment, charge circuit 304 is controlled by the state of a charge enable signal 307 provided to charge circuit 304 through pin 3 of electrical interface 310. This enables power management system 120 to control whether rechargeable battery pack 302 is recharged through the control of charge power 301 and/or charge enable signal 307.

It should be appreciated that incorporation of charge circuit 304 in rechargeable battery pack 302 may result in a battery pack that is greater in size, cost or complexity than conventional standard rechargeable battery packs. However, in accordance with the present invention, such a battery pack is compatible with appropriately configured devices, such as electrotherapy device 100. Such devices will be configured, as noted, with at least one power module receptacle 122 that accommodates rechargeable battery pack 102. Although rechargeable battery pack 302 may be larger than conventional battery packs, the use of battery pack 302 will enable electrotherapy device 100 to forego the implementation of a charge controller, thereby enabling any similarly configured battery pack 302 to be installed in the power module receptacle 122. In addition, considerable space savings in electrotherapy device 100 are achieved by integrating charge circuit 304 into self-contained rechargeable battery pack 302.

In one embodiment, rechargeable battery pack 302 includes a smart interface 306.

Smart interface 306 provides data regarding battery pack 302 to the device in which battery pack 302 is installed. In one embodiment described below, smart interface 306 is implemented to include an accessible memory module in which battery characteristics are stored. The battery data is provided to electrotherapy device through a data line 309 connected to pin 5 of interface 310. The data transfer is preferably bi-directional to enable electrotherapy device 100 to calculate or otherwise determine information that can then be communicated to and stored in smart interface 306. One embodiment of smart interface 306 is described in greater detail below.

Preferably smart interface 306 is powered by a power source other than battery 308 to insure availability of data regardless of the condition of battery 308. In addition, charger power 301 is not always available and, therefore, cannot be relied upon to provide the requisite power to smart interface 306. Accordingly, external power is preferably provided over line 313 to pin 7 of electrical interfaced 310. This power is provided by electrotherapy device 100, enabling smart interface 306 to operate even when the cells of battery 308 have little or no remaining available energy. As illustrated by the bi-directional arrow between smart interface 306 and charge circuit 304, charge circuit 304 may utilize data stored in smart interface 306 to generate a charge protocol to charge battery 308, and to store data in smart interface 306.

A battery status indicator 312 is also provided in rechargeable battery pack 302. Indicator 312 may be any type of one or more indicators now or later developed. For example, in one embodiment, indicator 312 is a press-to-test button that, when activated, accesses charge circuit 304 and smart interface 306 to make a status determination and to present such a determination to the operator. Press-to-test button preferably includes an LED that illuminates to provide an indication of the invoked test, although any technique may be implemented to communicate such information.

FIG. 3B is a schematic block diagram of an AC power pack 322 in accordance with one embodiment of the present invention. As noted, AC power pack 322 preferably has the same form factor as that of rechargeable battery pack 302. Accordingly, housing 372 is approximately the same size and configuration as housing 370, and electrical interface 330 has the same configuration as electrical interface 310. However, for reasons set forth below, electrical interface 330 preferably has pin assignments that are somewhat different than that of electrical interface 310.

DC power 321 is generated by AC power pack 322. DC power 321 includes V+ presented on line 323 through pin 1 and a ground voltage $V_{GND}$ presented on line 325 through pin 2 of interface 330. AC-to-DC converter 324 receives AC power 364 through an AC power electrical connector 334 connected to a corresponding receptacle 328. AC-to-DC converter 324 converts applied AC power 364 to DC power 321 suitable for use by electrotherapy device 100.

AC-to-DC power converter 324, also referred to as a phase-controlled converter, may be implemented in any well-known power electronics apparatus now or later developed. In one embodiment, AC-to-DC converter 324 is a silicon-controlled rectifier (SCR) implemented, for example, with thyristors. The structure and operation of AC-to-DC converter 324 is considered to be well known in the art and is not described further herein.

In embodiments wherein the form factor of AC power pack 322 is not the same as that of rechargeable battery pack 302, the size of AC power pack 322 impacts the design of a power module receptacle 122 that is designed to have power pack 322 installed therein. In those embodiments in which AC power pack 322 has the same form factor as rechargeable battery pack 302, then each power module receptacle 122 is preferably configured to receive either rechargeable battery pack 302 or AC power pack 322.

A power enable signal 361 provided over line 327 to pin 3 of interface 330 by power management unit 202 is utilized in certain embodiments of the present invention. As will be described below, such a power enable command signal can be used to control whether AC-to-DC converter 324 converts AC power to DC power, thereby controlling whether AC power 321 is available at pins 1 and 2 of electrical interface 330.

As with rechargeable battery pack 302 illustrated in FIG. 3A, AC power pack 322 may include a smart interface 306 that transmits and receives data and power over pins 5, 6 and 7. The remaining pins 4, 8 and 9 having connected thereto lines 361, 335 and 337, resepctively, are not used by AC power pack 322.

In one embodiment, a status indicator 332 is provided on a rear surface 339 of AC power pack housing 372. In this embodiment, status indicator 332 is visible to the operator when AC power pack 322 is installed in a power module receptacle 122. Status indicator 332 is required in certain regulating industries to provide the operator with an indication of whether AC power is currently supplied to the hosting device. Thus, status indicator 332 is illuminated when connector 334 connects AC power pack 322 to an AC power source. Otherwise, status indicator 332 is not illuminated. Additional status indicators may also be implemented.

FIG. 3C is a schematic diagram of a non-rechargeable battery pack 342 in accordance with one embodiment of the present invention. As noted, non-rechargeable battery pack 342 preferably has substantially the same form factor as that of rechargeable battery pack 302 and AC power module 322. Accordingly, housing 374 has approximately the same size and configuration of housing 170 and 372, and electrical interface 350 has the same configuration as electrical interfaces 310 and 330. However, electrical interface 350 may have different pin assignments than electrical interfaces 310 and 330.

Non-rechargeable battery pack 342 includes a smart interface 306 such as that described above with reference to rechargeable battery pack 302 and AC power pack 322. Smart interface 306 is allotted pins 5, 6 and 7 in electrical interface 350. In addition, battery 338 is allotted pins 8 and 9. As with battery 308 described above with reference to FIG. 3A, battery 338 provides a voltage V+ presented on line 335 through pin 8 and ground voltage $V_{GND}$ 357 presented on line 357 through pin 9 of electrical interface 350. Together, V+ 355 and $V_{GND}$ 357 comprise DC power 359.

As noted, the pin assignments of the three power modules may be different. For example, pins 8 and 9 of rechargeable battery pack 302 and non-rechargeable battery pack 342 provide DC power to device 100. On the other hand, DC power provided by AC power pack 322 is provided on pins 1 and 2 of electrical interface 330. The more reliable DC power provided by AC power pack 302 is managed differently than the DC power provided by battery packs 302 and 342. Identification of the source of power is easily achieved since device 100 can determine that there is no DC power available at pins 8 and 9 of AC power pack 322. Also, all three power modules have the same three pins 5, 6 and 7 assigned to smart interface 306, allowing device 100 to be configured to always communicate over the same pins in each of the receptacles 122.

Other features of the illustrated pin assignments include the use of pins 1 and 2 of rechargeable battery pack 302 to provide DC power 301 while those same pins of non-rechargeable battery pack 342 are unassigned. This avoids an inadvertent attempt to charge non-rechargeable battery pack 342 which, as is well known, can cause serious damage to electrotherapy device 100. Thus, while providing commonality across electrical interfaces 310, 330 and 350, such as with pins 5–7, variations may be implemented to achieve safety, efficiency or other objectives.

In addition, although the same form factor is preferably implemented across all three power modules 302, 322 and 342, appropriate mechanical keying may be included in electrotherapy device 100 to insure proper orientation of each power module 102 when installed in a power module receptacle 122. Furthermore, additional keying may be provided to avoid two AC power packs from simultaneously supplying power to electrotherapy device 100 as such an arrangement may cause damage to the device 100, installed AC power packs 322 or other installed battery packs 302, 342.

For example, only one receptacle 122 may include a wall with an aperture that aligns with plug receiver 328 on AC power pack 322 so that receiver 328 can have a connector 334 inserted therein while AC power pack 322 is installed in that receptacle. It should be understood, however, that there are numerous embodiments that can be implemented. For example, ribs or some other surface feature may be included in AC power pack 322 that are absent from rechargeable and non-rechargeable battery packs 302, 342. Power module receptacle 122A, then, would include corresponding slots to accept the ribs while power module receptacle 122B would not include such slots.

Figure 4:
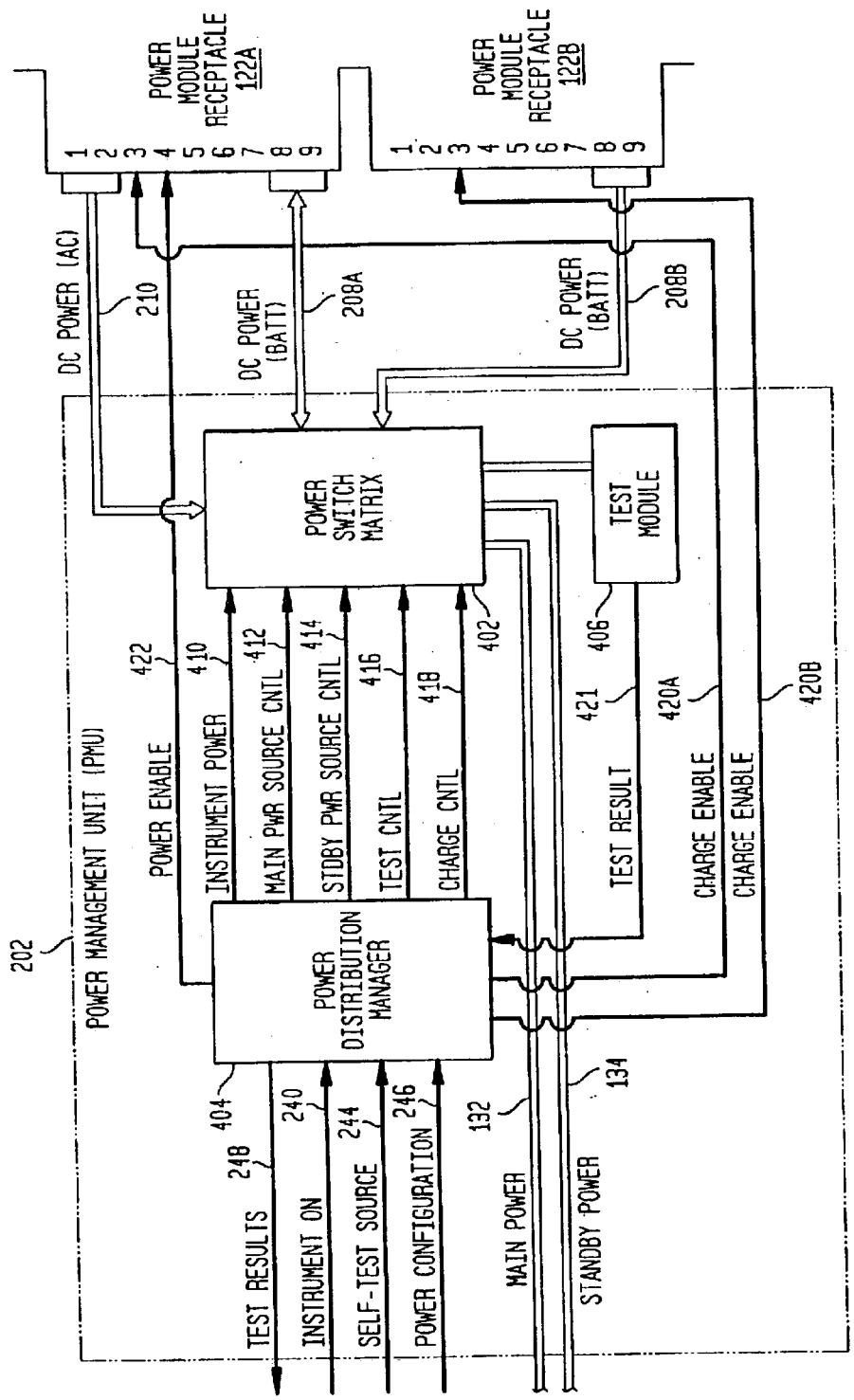
FIG. 4 is a block diagram of the principal elements of one embodiment of the power management unit illustrated in FIG. 2.

FIG. 4 is functional block diagram of one embodiment of power management unit 202 illustrated in FIG. 2. As noted, power management unit 202 manages the distribution of power provided at one or more power module receptacles 122 to electrotherapy device 100. Preferably, this distribution of power includes the distribution of a DC charging power to one or more power module receptacles 122. In the illustrative embodiment, a power configuration is achieved through the selected interconnection of power buses 208A, 208B and 210 from power module receptacles 102 and at least one of the internal device power buses 132, 134.

Power management unit 202 primarily includes a power switch matrix 402 and a power distribution manager 404. Power switch matrix 402 connects power buses from power module receptacles 122 with individual internal power buses that ultimately provide device power. The state of the switches in power switch matrix 402 define a current power configuration and are controlled by power distribution manager 404. In this illustrative embodiment, instrument controller 106 (shown in FIG. 1) determines the power configuration based on one or more of the following factors: the number, type and other characteristics of installed power modules 102, the characteristics of the application, such as the use model, of the electrotherapy device 100, among others. The power configuration 246 is provided to power distribution manager 404 in the form of one or more commands. Power distribution manager 404 then controls the state of the power switch matrix 402 to implement the specified power configuration.

In addition to power configuration 246, instrument controller 106 also generates "instrument on" signal 240, described above, that which indicates whether electrotherapy device 100 is to be powered. Power distribution manager 404 also receives a self-test source command 244 to identify which installed power module 102 is to provide power during a particular self-test.

To implement a power configuration, a number of switch control commands may to be generated by power distribution manager 404 to configure power switch matrix 402 and, in certain embodiments, for controlling installed power modules 102. As shown in FIG. 4 there are five commands generated by this embodiment of power distribution manager 404 to control the configuration of power switch matrix 402. In this illustrative embodiment, the configuration of power switch matrix 402 relates to three power functions: (1) providing power to electrotherapy device 100; (2) recharging rechargeable battery packs 302; and (3) testing selected power modules 102. It should be understood that other power functions may also be supported by the present invention.

With regard to providing power to electrotherapy device 100, instrument power command 410, main power source control command 412 and standby power source control command 414 are generated to control whether main and/or standby instrument power is applied to electrotherapy device 100 and, if so, by which power module 102.

With regard to charging rechargeable battery packs, a charge control command 418 is generated by power distribution manager 404 to configure power switch matrix 402 so as to route power provided by an AC power pack 322 installed in receptacle 122A to a rechargeable battery pack 302 installed in receptacle 122B. Similarly, a test control command 416 is generated by power distribution manager 404 to configure power switch matrix 402 to apply a selected power module 102 to test module 406. The structure and operation of power switch matrix 402 in response to these commands is described in detail below with respect to FIG. 5.

In addition to the control commands provided to power switch matrix 402, power distribution manager 404 may also generate commands for controlling power modules 102. These commands are provided in certain embodiments only and may be in place of or in addition to commands provided to power switch matrix 402. These include charge enable commands 420A and 420B that enable or disable rechargeable battery packs 302 installed in power module receptacles 122A and/or 122B to charge internal battery 308. A power enable control command 422 is provided to power module receptacle 122A to control the conversion of AC power to DC power by an AC power pack 322 installed therein. Additional or alternative commands may be included in other embodiments of the invention.

Figure 5:
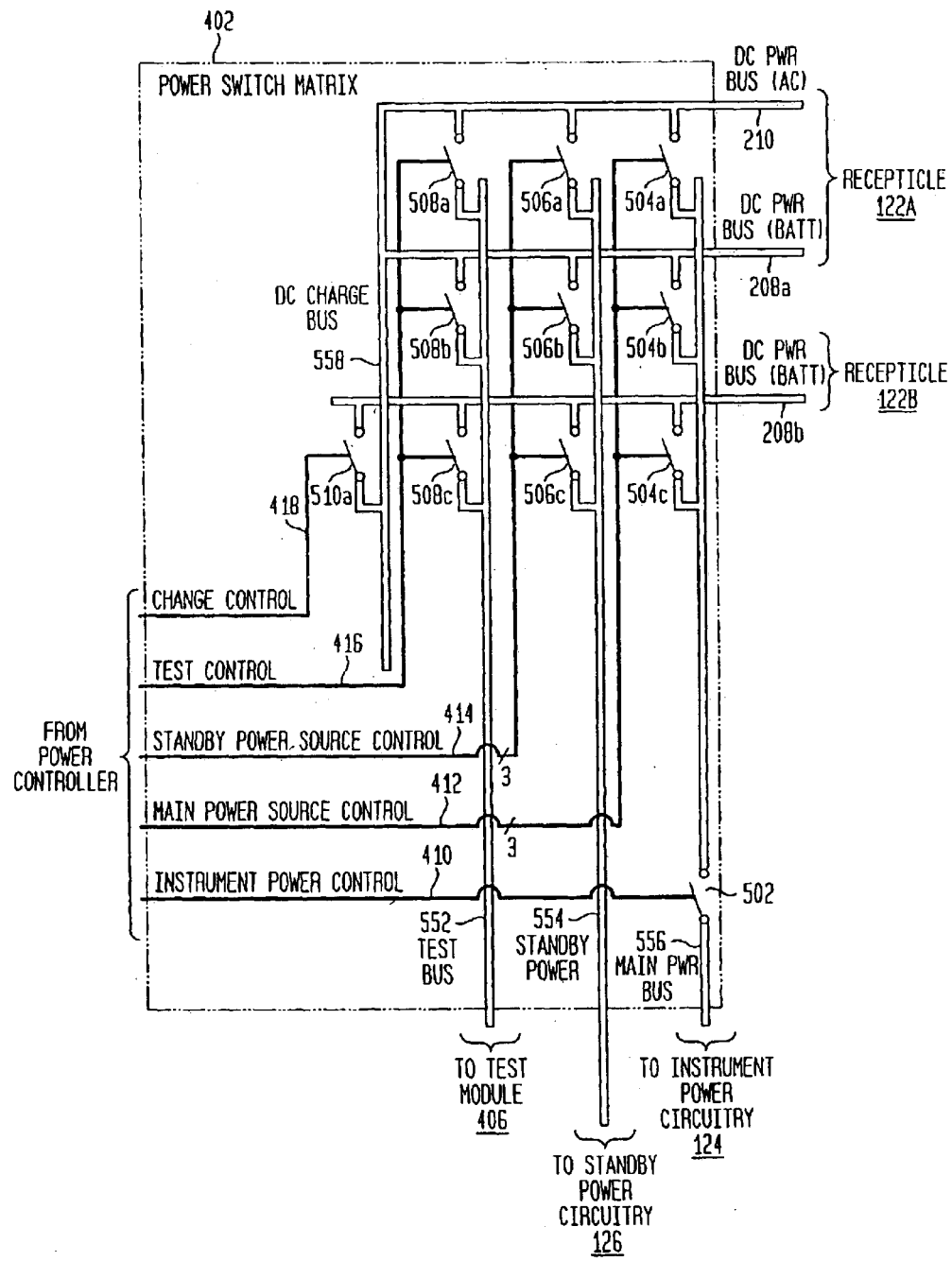
FIG. 5 is a schematic diagram of one embodiment of the power switch matrix illustrated in FIG. 4.

FIG. 5 is a schematic diagram of one embodiment of power switch matrix 402. As noted, in response to power distribution manager 404, power switch matrix 402 connects each power bus 208A, 208B and 210 from power module receptacles 122 to none, one, or multiple internal power buses to achieve a desired power configuration. In the illustrative embodiment, a power configuration that provides main instrument power, standby power, rechargeable battery pack charging power and/or power module testing configurations may be achieved. However, it should be understood that additional internal power buses or a single main instrument power bus may be provided in alternative embodiments.

To provide flexibility in terms of which input power buses 208A, 208B and 210 are connected to which internal buses 552–558, the illustrated matrix arrangement of the internal and input buses is provided. For ease of illustration, the three input power buses 208A, 208B and 210 are arranged horizontally while the four internal power buses 552–558 are arranged vertically.

At each intersection or cross over of an input and internal bus there is an independently-controllable switch to electrically connect the two buses. In the illustrative embodiment, the switches are shown schematically. It should be appreciated that any type of switch suitable for switching the voltages carried on the buses may be used. For example, high voltage field effect transistors (FET), relay switches and the like may be used.

Power switch matrix 402 receives as inputs three power buses connected to power module receptacles 122. Power bus 210 carries DC power from an AC power pack 322 installed in power module receptacle 122A. As noted, mechanical keying or some other restrictive measure may be implemented to prevent AC power module 322 from providing power to electrotherapy device 100 when installed in receptacle 122B. In this case, only one DC power line from an installed AC power pack 322 is provided; no corresponding bus is provided for receptacle 122B. In addition, power lines 208A and 208B carry DC power from a rechargeable or non-rechargeable battery pack 302, 342 installed in power module receptacle 122A and 122B, respectively.

There are four internal power buses in this embodiment of power switch matrix 402. The internal power buses include a main power bus 556 and a standby power bus 554. These buses exit power switch matrix 402 to provide main power 132 and standby power 134, respectively, to power distribution network 140, as described above. In addition, there is a DC charge bus 558 that provides DC power to a rechargeable battery pack 302 installed in power module receptacle 122B. As shown in FIG. 5, DC charge bus 558 is connected to DC power bus 210 received from power module receptacle 122A. As noted, DC power bus 210 carries DC power provided by an AC power pack 322 installed in receptacle 122A. Thus, the source of DC power for charging an installed rechargeable battery pack in receptacle 122B is an AC power pack 322 installed in receptacle 122A. Finally, in certain embodiments, there is a test bus 552 that exits power switch matrix 402 and is connected to test module 406.

There are three main power switches 504A–504C operable to connect the three input buses 208A, 208B and 210 to internal main power bus 556. Switches 504 may be operated to select which of the installed power modules 102 will be used to provide main power 132. There are three main power source control lines 412 received from power controller 406. Each main power source control line 412 carries a signal that controls one main power switch 504.

Similarly, there are three standby power switches 506A–506C operable to connect the three input buses 208A, 208B and 210 to internal standby power bus 554. Switches 506 may be operated to select which of the installed power modules 102 will be used to provide standby power 132. There are three standby power source control lines 414 received from power controller 406. Each standby power source control line 414 carries a signal that controls one standby power switch 506.

Likewise, there are three switches 508A–508C that may be operated to connect the three input buses 208A, 208B and 210 to internal test bus 552. Three test control lines 416 each controlling one of the switches 508 are received from power distribution manager 404. Switches 508 are operated to select which of the installed power modules 102 will be tested by test module 406.

Also, there is a switch 510A operable to connect DC charge bus 558 to DC power line 208B to provide DC power to power module receptacle 122B. As noted, the source of DC power for charge bus 558 is DC power line 210 received from receptacle 122A. This enables received DC power to be used to charge a rechargeable battery pack installed in receptacle 122B when there is an AC power pack 322 installed in receptacle 122A.

Finally, there is a switch 502 that connects main power bus 556 to instrument power circuitry 124. Instrument power control signal 410 controls switch 502. When instrument power is to be provided to electrotherapy device 100, instrument power control signal 410 is generated to cause switch 502 to close, connecting internal main power bus 556 to power distribution network 140. This provides a redundant switch to control main instrument power.

Figure 6:
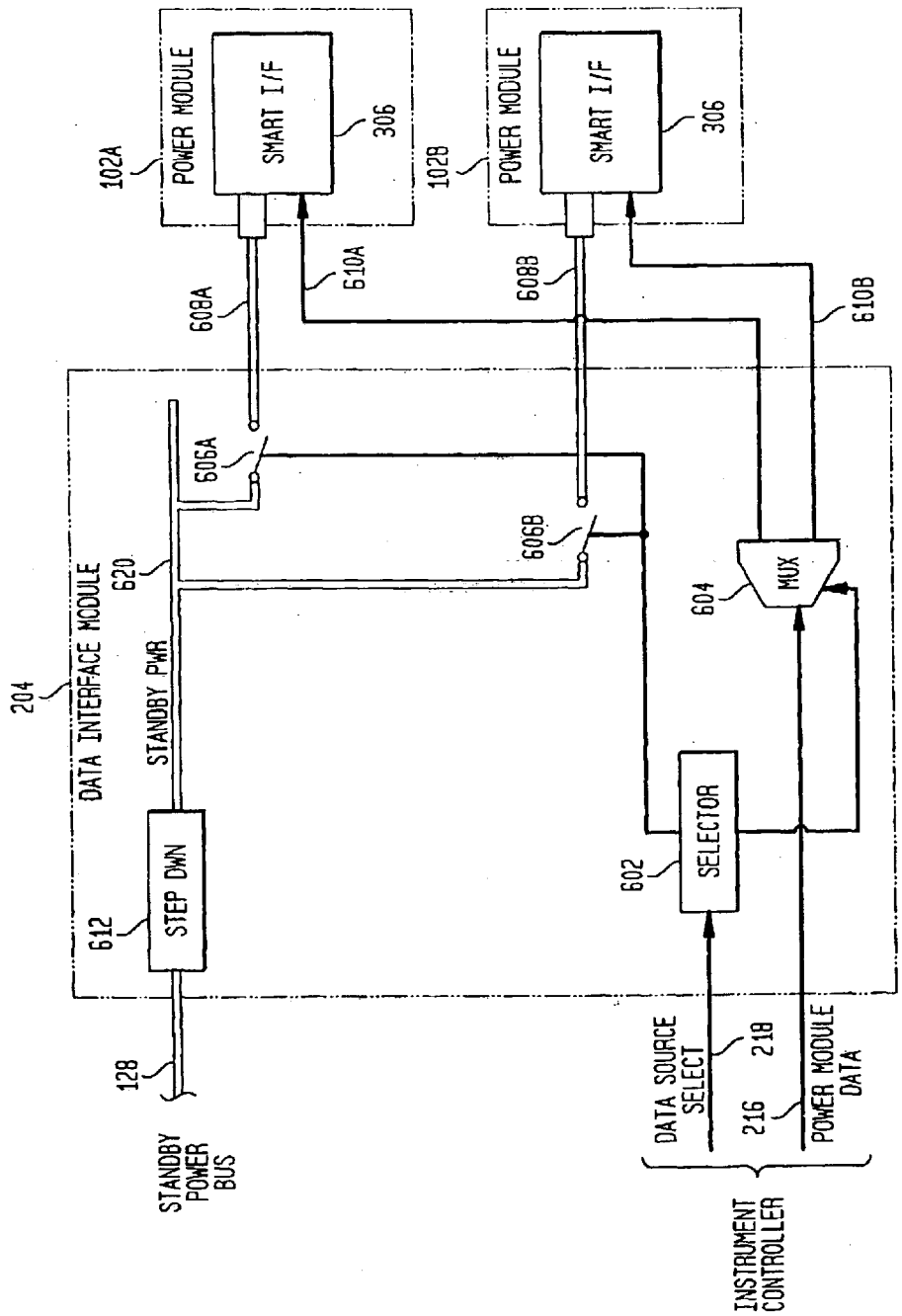
FIG. 6 is a block diagram of the data interface module illustrated in FIG. 2.

FIG. 6 is a schematic block diagram of data interface module 204. As noted, data interface module 204 transfers data between installed power modules 102 and instrument controller 106 or, in alternative embodiments, directly to power management unit 202. As introduced above with reference to FIGS. 3A–3C, each power module 102 has installed therein a smart interface 306. In the illustrative embodiment, smart interface 306 includes a memory accessible by data interface module 204 to retrieve data for subsequent use by power management unit 202 in determining the power configuration, as well as to store data in smart interface 306.

As noted, smart interface 306 resides in power modules 102 and is preferably powered by electrotherapy device 100 rather than the hosting power module 102. This insures power availability for smart interface 306 regardless of battery pack or AC power pack conditions. In addition, data interface module 204 preferably uses standby power 128 for providing power to smart interface 306. Standby instrument power 128 is preferably available continuously as compared with main instrument power. Thus, in this illustrative embodiment, data interface module 204 is connected to standby power bus 128. A step-down transformer 612 may be used to reduce the DC voltage provided on standby bus 128 to a standby power level 620 suitable for smart interface 306. Power lines 608A, 608B are provided to each power module 102A and 102B, respectively, to provide power to smart interface 306. This power is received at pins 6 and 7 of the standardized interface, as shown in FIGS. 3A–3C.

Data interface module 204 includes two separately controllable switches 606A and 606B to connect individual power lines 608A and 608B to standby power bus 128. Implementation of individual switches allows standby power bus 128 to be applied selectively to each smart interface 306. This arrangement can be used to minimize the power consumption of smart interfaces 306. For example, only the smart interface 306 with which data is being transferred need by powered. The remaining smart interface 306 may remain without power. A selector 602 receives data source select signal 218 from instrument controller 106 and operates the appropriate switch 606 accordingly to connect standby power bus 128 to a desired power line 608 thereby providing power to a desired smart interface 306.

Data lines 610A and 610B connect smart interface 306 of each power module 102 with data interface module 204. As noted with reference to FIGS. 3A–3C, the bi-directional data line is connected to pin 5 of each power modules 102. For rechargeable battery pack 302, this is line 309 connected to pin 5 of electrical interface 310; for AC power pack 322 this is data line 329 connected to pin 5 of electrical interface 330; and for non-rechargeable battery pack 342 this is data line 349 connected to pin 5 of electrical interface 350. It should be appreciated that such data lines 610 may take on any form such as a data bus, multiple discrete data lines and the like.

The data lines 610A and 610B are received as inputs into a bi-directional multiplexer 604. A power module data line 216 connects multiplexer 604 with instrument controller 106. Selector 602 selects which of data line 610A, 610B is to be connected to power module data line 216 to support bi-directional data traffic between instrument controller 106 and a smart interface 306. Selector 602 makes such a determination based on data source select signal 218 provided by instrument controller 106.

Smart interface 306 may be implemented in any circuitry now or later developed. Referring to the particular implementation illustrated in FIG. 7, smart interface 306 is implemented in the model DS243X family of battery identification chips available from Dallas Semiconductor Corporation, Dallas, Tex. In the particular embodiment illustrated in FIG. 7 a model DS2434 Battery Identification Chip 702 and a model DS2480 line driver 704 from Dallas Semiconductor Corporation, Dallas Tex., USA are integrated into power modules 102.

The structure and operation of the DS2434 and DS2480 (as well as the other devices in the DS243X family) are described in detail in their respective data sheets, including the Dallas Semiconductor DS2434 Battery Identification Chip data sheet, and the Dallas Semiconductor DS2480 Serial I-Wire Line Driver data sheet, as well as Dallas Semiconductor, "Tech Brief No. 5: Programming DS243X Battery Identification Chips" by Norbert Wank, all of which are available from Dallas Semiconductor Corporation, Dallas, Tex. (http://www.dalsemi.com). Accordingly, the features of battery identification chip 702 are described only briefly herein.

The Dallas Semiconductor DS243X family of Battery Identification Chips provides a convenient method for storing battery characteristics such as battery life, chemistry, charge/discharge characteristics, etc., in volatile or nonvolatile memory. In addition, a relatively simple method for tagging and identifying battery packs by manufacturer, battery chemistry or other identifying battery characteristics is optionally provided. The exemplary DS2434 battery identification chip 702 provides a unique 1-Wire™ interface port 706 ("1-Wire" is a registered trademark of Dallas Semiconductor Corporation, Dallas, Tex.). The use of such an interface reduces the number of output connectors that need to be implemented on battery ID chip 702.

Battery identification chip 702 includes non-volatile Memory (NVRAM) 708A, 708B and static RAM (SRAM) 710A, 710B. In this specific embodiment, there are four special-purpose registers included in battery identification chip 702. NVRAM 708B includes two registers 712, 714 to retain the ID number for the chip and the cycle count, respectively. SRAM 710B includes registers 716, 718 that contain the measured temperature value and status registers for the device.

Battery identification chip 702 includes a scratchpad memory 720 including two 256 bit memory regions 722A, 722B for communicating with a 256-bit region of NVRAM 708A and a 256-bit region of SRAM 710A, respectively. Scratchpad memory 722A, 722B is used to insure data integrity when communicating over the 1-Wire bus 724. Data is first written to the scratchpad 720 where it can be read back. After the data has been verified, a copy scratchpad command will transfer the data to the SRAM 710A or NVRAM 708A. This process insures data integrity when modifying the contents of memory.

It should become apparent from the present disclosure that power module data 216 may be provided to power management system 120 by installed power modules 102 using other techniques, systems or methodologies. For example, in one alternative embodiment, smart interface 306 is implemented as an electrical circuit. In such an embodiment, the data 216 may be represented by electrical features of the circuit such as the resistance provided by one or more resistors. The circuit can generate signals indicative of specific characteristics or data interface module 204 can poll it in some well-known manner. In another embodiment, mechanical interface features may represent the power module data 216. For example, one approach that may be used is disclosed in U.S. patent application Ser. No. 09/191,685, entitled "Battery Pack Chemistry Detection and Identification System and Method," and/or Ser. No. 09/192,116, entitled "System and Method for Detecting Performance Components of a Battery Pack," both of which were filed Nov. 13, 1998, the disclosures of which are incorporated by reference herein in their entirety. A still further alternative is to use a sense cell as described in U.S. Pat. No. 5,483,165 to Cameron et al., entitled "Battery System and Method For Determining A Battery Condition," the disclosure of which is incorporated by reference herein in its entirety. Other implementations of battery characteristic identifier 122 may be implemented, for example, as part of a smart battery label as described in commonly-owned U.S. patent application Ser. No. 09/184,485 filed Nov. 2, 1998, entitled "A Conforming Intelligent Battery Label," the specification of which is incorporated herein by reference. The approach selected to communicate data 216 to system 120 ultimately depends upon the number of battery characteristics, the number of values each battery characteristic may assume, whether the battery characteristics are determined at time of manufacture (such as battery chemistry) or are determined dynamically (such as current battery capacity), the structure and function of battery pack 102 and battery-powered device 100, etc., among other factors. The consideration of these and other factors is considered to be within the purview of those of ordinary skill in the art.

Figure 8A:
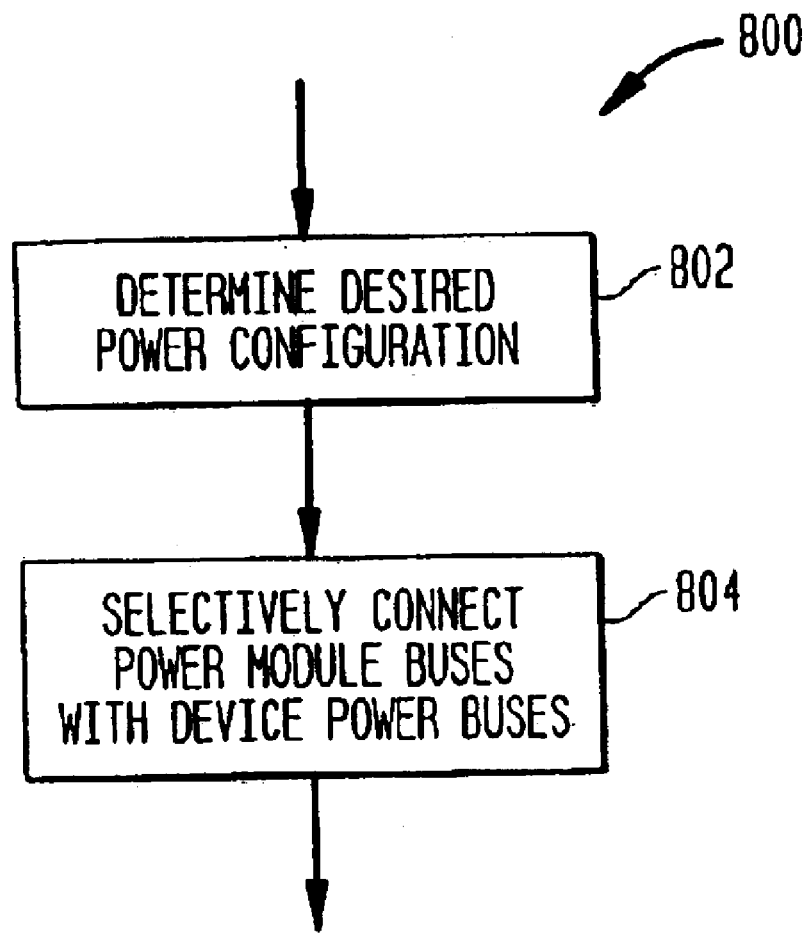
FIG. 8A is a flow chart of the processes performed to establish a power configuration in accordance with one embodiment of the present invention.

FIG. 8A is a flow chart of the processes performed to establish a power configuration in accordance with one embodiment of the present invention. At block 802 the desired power configuration for electrotherapy device 100 is determined. At block 804 power management system 120 selectively connects input power buses with device power buses to effect the desired power configuration.

Figure 8B:
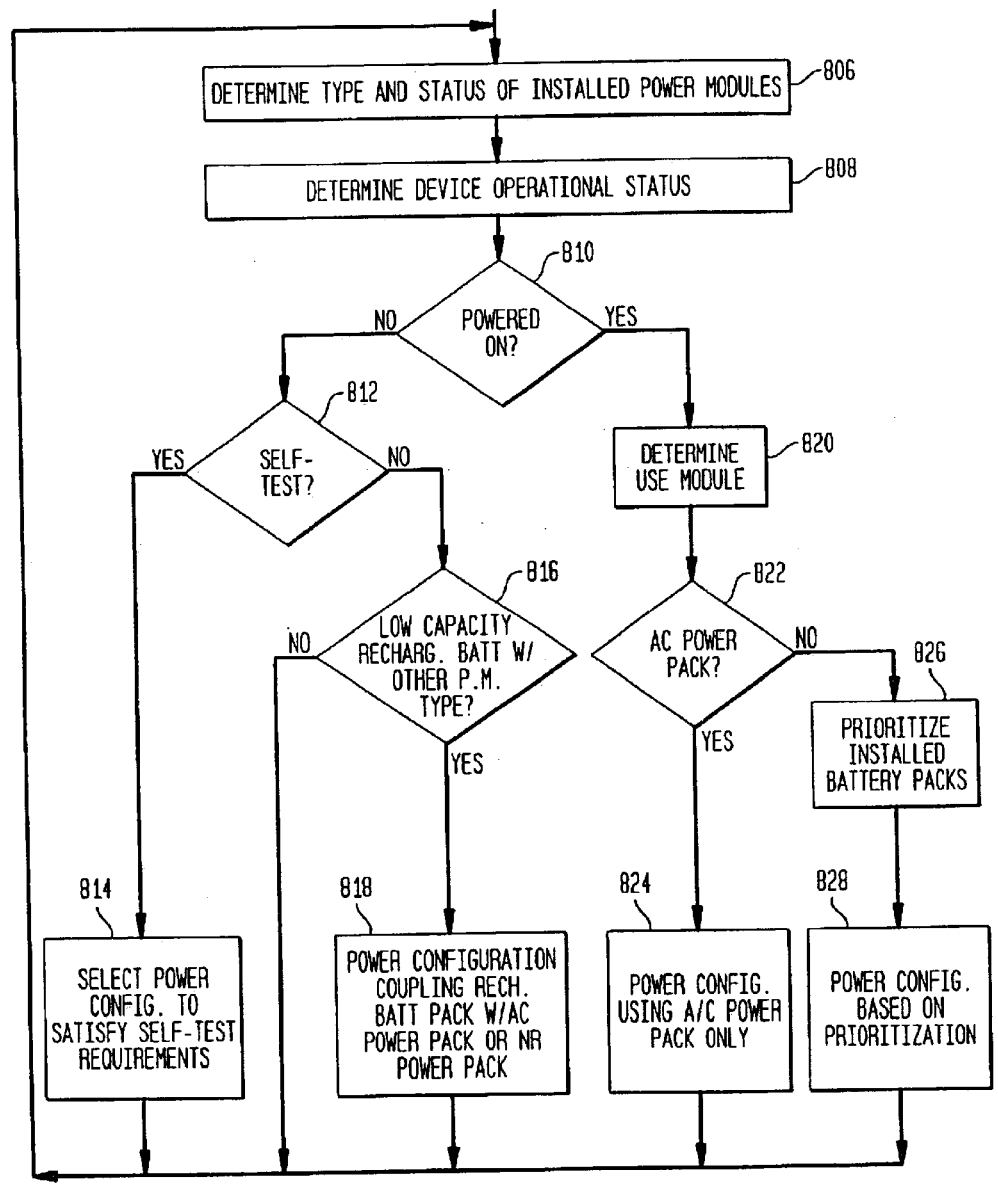
FIG. 8B is a flow chart of the processes performed at block 802 of FIG. 8A.

FIG. 8B is a flow chart of the processes performed at block 802 of FIG. 8A. At block 806, instrument controller 106 determines the type and status of installed power modules 102. There may be any combination of power module types installed in power module receptacles 122 at any given time. In addition, the status of the installed power modules 102 may include a rechargeable or non-rechargeable battery pack having any capacity, an AC power pack that may or may not be able to supply DC power, etc.

At block 808, the operational state of electrotherapy device 100 is determined. If electrotherapy device 100 is determined to not be powered off at block 810, then processing continues at block 812 at which the self-test status is determined. If device 100 is performing a self-test, then the selected power configuration will connect the power module 102 required for that self-test to the indicated internal power bus. For example, if the self-test requirements call for testing an installed non-rechargeable battery is pack 342 installed in power module receptacle 122B, then the selected power configuration will include the connection of the power bus 208C from power module receptacle 122B to the desired internal power bus, such as main power bus 132.

Alternatively, if no self-test is currently being performed, then it is determined whether the installed power modules 102 include a rechargeable battery pack 302 that has a capacity sufficiently low to warrant recharging, as well as a second installed power module 102 that can provide the requisite charging power. In the embodiment described above, the power module that can provide the DC charging power can only be an AC power pack 322 installed in power module receptacle 122A. If such a condition exists, then the selected power configuration is set at block 818 to include the electrical coupling of these two installed power modules 102.

If at block 810 it is determined that device 100 is powered on, then the use model of the device is determined at block 820. As noted, this may be a value generated by internal controller 106 or it may be inferred from the type of power modules 102 installed in power module receptacles 122. With the given use model it is determined at block 30 822 whether one of the installed power modules 102 includes an AC power pack 322. If so, then processing continues at block 824 at which the power configuration is selected to power device 100 with AC power pack 322 only. Other installed power modules 102, if any, would include a rechargeable or non-rechargeable battery pack 302, 342. These power modules 102 are not used to power device 100 so as to conserve their stored energy.

If it is determined at block 822 that there is no AC power pack 322 installed in power module receptacle 122A, then processing advances to block at which the installed battery packs, if more than one, are prioritized based on their current capacity, anticipate device use module and other factors. The power configuration is then established at block 828 based on this prioritization scheme. The process is periodically repeated as shown by the return arrow to block 806.

FIG. 9 is a table illustrating the different combinations of power modules 102 that may be concurrently installed in power module receptacles 122 when a two receptacle embodiment is employed. In this example there are two power module receptacles 122A and 122B. However, it should be appreciated by those of ordinary skill in the art that more than two modules can be employed without deviating from the scope of the invention.

Power module receptacle 122B is restricted to having installed therein battery packs only; that is, AC power pack 322 cannot be installed in receptacle 122B. The various combinations can be implemented for any reason, some of which have been noted above. In this example, the inferred or anticipated use module of the device is considered in determining the power configuration. Take, for example, combination 901, which was noted above. An AC power pack 322 is installed in receptacle 122A while a rechargeable battery pack 302 is installed in receptacle 122B. For the reasons noted above, instrument controller 106 infers that device 100 will be used in accordance with the high use model due to the presence of rechargeable battery pack 302. Instrument controller 106, therefore, would instruct power management system 120 to implement a power configuration such that rechargeable battery pack 302 is utilized as the primary power source and AC power pack 322 as the back-up power source. This arrangement may be desired because rechargeable battery pack 302 enables capacitor 108 to charge faster when preparing to deliver a shock. To implement this power configuration, power management system 120 connects rechargeable battery pack 302 to main and standby power buses 132, 134 by closing switches 504C and 506C.

AC power pack may be used for performing monitoring functions thereby conserving the energy stored in rechargeable battery pack 302. In addition, AC power pack 322 may also serve as a backup power source should rechargeable battery pack 302 become depleted. To replace rechargeable battery pack 302 with AC power pack 322 as the primary power source in device 100, power management system 120 opens switches 504C and 506C and closes switches 504A and 506A. In addition, when device 100 is not in use, AC power pack 322 can be connected to rechargeable battery pack 302 by activating switch 510A. This, as noted, connects DC power bus 208B from receptacle 122B to DC charge bus 558, which originates with DC power bus (AC) 210 from receptacle 122A. Rechargeable battery pack 302 then recharges for a future deployment.

Another example is combination 904 wherein a rechargeable battery back 302 is installed in receptacle 122A while a non-rechargeable battery pack 342 is installed in receptacle 122B. Here, instrument controller 106 would infer that device 100 will be used in accordance with the high use model due to the presence of rechargeable battery pack 302. Instrument controller 106, therefore, would instruct power management system 120 to implement a power configuration such that rechargeable battery pack 302 is utilized as the primary power source and non-rechargeable battery pack 342 as the back-up power source in the event of a catastrophic power failure. The switches in power switch matrix 402 may be open and closed accordingly.

It should be understood that various changes and modifications of the embodiments shown in the drawings and described in the specification may be made within the spirit and scope of the present invention. For example, it should be apparent to those of ordinary skill in the art that the device in which the power modules are installed may be any type of device with any number of power module receptacles 122. As another example, although in the embodiments of the invention described herein the power module data is provided by the installed power modules, the invention is not limited to such embodiments. Rather, the invention contemplates that such information may be provided elsewhere including, for example, from instrument controller 106, through an operator control input, etc. Also, in the illustrative embodiment, power management system 120 is responsive to instrument controller 106. However, power management 120 may itself include the necessary processor and logic to perform the power distribution operations noted as being associated with instrument controller 106. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A set of power modules for providing a DC voltage to a device when one or more of the power modules is installed therein, the set of power modules comprising:

a rechargeable battery pack including a first housing, one or more rechargeable battery cells and a battery charger mounted within the first housing, wherein the battery charger applies a charging voltage to the battery cells, the charging voltage being derived from an externally-applied DC voltage, and wherein the rechargeable battery cells generate a first DC voltage suitable for use by the device;

a non-rechargeable battery pack including a second housing and one or more non-rechargeable battery cells mounted within the second housing, wherein the non-rechargeable battery cells provide a second DC voltage suitable for use by the device; and an AC power pack including,
   a third housing,
   an AC-to-DC converter mounted within the third housing, and
   an electrical interface for providing an externally-applied AC voltage to the AC-to-DC converter, wherein the AC-to-DC converter converts the applied AC power to a third DC voltage suitable for use by the device,
      wherein the electrical interfaces for the rechargeable battery pack and the non-rechargeable battery pack and the AC power pack have different pin assignments within the same configuration.

2. The set of power modules of claim 1, wherein the first, second and third housings have a same form factor.

3. The set of power modules of claim 1, wherein the rechargeable battery pack, the non-rechargeable battery pack and the AC power pack each have a same electrical interface for interfacing with the device.

4. The set of power modules of claim 1, wherein a portion of the rechargeable battery pack electrical interface at which the first DC voltage is provided is the same as a portion of the non-rechargeable battery pack electrical interface at which the second DC power is presented.

5. The set of power modules of claim 1, wherein the rechargeable battery pack, the non-rechargeable battery park and the AC power pack, each further comprising a smart interface mounted within the first, second and third housings, respectively, wherein the smart interface provides externally data pertaining to the respective power module, and further wherein each of the rechargeable battery pack, the non-rechargeable battery pack and the AC power pack is configured such that the smart interface is powered by the device.

* * * * *